(12) United States Patent
Chez

(10) Patent No.: US 9,925,244 B1
(45) Date of Patent: Mar. 27, 2018

(54) TREATMENT OF WARTS IN NON-IMMUNOSUPPRESSED PATIENTS

(71) Applicant: Michael Chez, Granite City, CA (US)

(72) Inventor: Michael Chez, Granite City, CA (US)

(*) Notice: Subject to any disclaimer, the term of this patent is extended or adjusted under 35 U.S.C. 154(b) by 0 days.

(21) Appl. No.: 15/045,294

(22) Filed: Feb. 17, 2016

Related U.S. Application Data

(60) Provisional application No. 62/117,119, filed on Feb. 17, 2015.

(51) Int. Cl.
| | | |
|---|---|---|
| *A61K 38/19* | (2006.01) | |
| *A61K 35/28* | (2015.01) | |
| *A61K 35/51* | (2015.01) | |
| *A61K 9/00* | (2006.01) | |

(52) U.S. Cl.
CPC .......... *A61K 38/193* (2013.01); *A61K 9/0019* (2013.01); *A61K 35/28* (2013.01); *A61K 35/51* (2013.01)

(58) Field of Classification Search
CPC .................................................. A61K 9/0019
See application file for complete search history.

(56) References Cited

U.S. PATENT DOCUMENTS

| | | |
|---|---|---|
| 7,456,224 B2 | 11/2008 | Chez |
| 7,709,213 B2 | 5/2010 | Chez |
| 7,785,601 B2 | 8/2010 | Schaebitz et al. |
| 8,084,421 B2 | 12/2011 | Lopez et al. |
| 8,236,306 B2 | 8/2012 | Tobinick |
| 8,354,438 B2 | 1/2013 | Chez |
| 8,372,397 B2 | 2/2013 | Moon et al. |
| 8,431,538 B2 | 4/2013 | Kozikowski |
| 8,524,655 B2 | 9/2013 | Zhao et al. |
| 8,545,812 B2 | 10/2013 | Hong et al. |
| 8,613,929 B2 | 12/2013 | Gaillard et al. |
| 8,741,847 B2 | 6/2014 | Chez |
| 2002/0198150 A1 | 12/2002 | Chajut |
| 2008/0292597 A1 | 11/2008 | Steenblock |
| 2011/0060266 A1 | 3/2011 | Streeter et al. |
| 2011/0104100 A1 | 5/2011 | Riordan et al. |
| 2012/0231065 A1 | 9/2012 | Schaebitz et al. |
| 2013/0028870 A1 | 1/2013 | Royal et al. |
| 2013/0281484 A1 | 10/2013 | Kozikowski et al. |
| 2014/0005071 A1 | 1/2014 | Chappell et al. |
| 2014/0056842 A1 | 2/2014 | Sackner-Bernstein et al. |
| 2014/0065162 A1 | 3/2014 | Lipson et al. |

FOREIGN PATENT DOCUMENTS

| | | |
|---|---|---|
| EP | 2 186 252 A2 | 5/2010 |
| WO | 2003061685 A1 | 7/2003 |
| WO | 2008031448 A1 | 3/2008 |
| WO | 2010051335 A1 | 5/2010 |

OTHER PUBLICATIONS

Chernoff et al. teach (2002, Protein-Protein Interactions: A Molecular Cloning Manual, Cold Spring Laboratory Press, Chapter 2, pp. 7-13).*
Kortesidis et al. (2005, Blood, vol. 105, pp. 3793-3801).*
Gimble et al., 2003, Cytotherapy, vol. 5(5), pp. 362-369.*
Johansson et al., 1999, Experimental Cell Res., vol. 253, pp. 733-736.*
Eggenhofer et al. (2014, Frontiers in Immunology, vol. 5(148), pp. 1-6).*
Guillot et al. (2007, J. Cell. Mol. Med., vol. 11(5), pp. 935-944).*
Lakshmipathy et al. (2005, Blood Rev., vol. 19, pp. 29-38).*
Lindvall et al., 2003, Pharmacology Res., vol. 47, pp. 279-287.*
Liu et al. (2012, Blood, vol. 120(1), pp. 181-189).*
Tagami et al. (1980, Cancer, vol. 45, pp. 2557-2563).*
Sinal et al. (2005, Semin. Pediatr. Infect. Dis., vol. 16, pp. 306-316).*
Neupogen Administration Guildelines from the manufacture Amgen, 43 pages in length.*
Gardellini, A, et al., "Filgrastim XM02 (Tevagrastim) after autologous stem cell transplantation compared to enograstim: favourable cost-efficacy analysis," Ecancer Medical Science, Jun. 25, 2013.
Chez, et al.: "Immune Therapy in Autism: Historical Experience and Future Directions with Immunomodulatory Therapy," Neurotherapeutics: The Journal of the American Society for Experimental NeuroTherapeutics, Jul. 2010, 293-301, vol. 7.
Jensen, et al.: "First Autologous Cell Therapy of Cerebral Palsy Caused by Hypoxic-Ischemic Brain Damage in a Child after Cardiac Arrest-Individual Treatment with Core Blood," Case Reports in Transplantation, 2013.
Connolly, A., et al.: "Serum autoantibodies to brain in Landau-Kleffner variant, autism, and other neurologic disorders," 1999, Department of Neurology and Pediatrics, Washington University et al.
Grigg, AP.,: "Optimizing dose and scheduling of filgrastim (granulocyte colony-stimulating factor) for mobilization and collection of peripheral blood progenitorcells in normal volunteers," Blood, 1995, 4437-4445, 86.
Connolly, A., et al.: "Brain-Derived Neurotrophic Factor and Autoantibodies to Neural Antigens in Sera of Children with Autistic Spectrum Disorders, Landau-Kleffner Syndrome, and Epilepsy," Society of Biological Psychiatry, 2005.
Chez, M., MD., : "Autologous Umbilical Cord Blood Treatment for Autism: Rationale and Potential Goals of Treatment," Practical Neurology, 2013.
Jensen, A.,: "Autologous Cord Blood Therapy for Infantile Cerebral Palsy: From Bench to Bedside," Obstetrics and Gynecology International, 2014, vol. 2014.
Sun, J., et al: "Cord blood for brain injury," Cytotherapy, 2015, 1-11.

(Continued)

*Primary Examiner* — Thaian N Ton
*Assistant Examiner* — David A. Montanari
(74) *Attorney, Agent, or Firm* — Cahn & Samuels, LLP

(57) ABSTRACT

A method for treating warts includes administering to a patient with warts a composition having an autologous, matched allogenic, donor tissue source of mixed, hematological, pleuripotent, ISPC derived or harvested or induced mesenchymal type stem cells and/or filgrastim, derivatives, bioequivalents, and pharmaceutically effective salts thereof. Patients include both non-chemotherapy or non-immunosuppressed patients, as well as chemotherapy or immunosupressed patients with warts of non-responsive cutaneous type. The treatment leads to resolution of warts and/or a change in their response to laser therapy or standard treatments previously shown not to be effective.

8 Claims, 4 Drawing Sheets

(56) References Cited

OTHER PUBLICATIONS

Papadopoulos, K., et al: "Safety and feasbility of autologous umbilical cord blood transfusion in 2 toddlers with cerebral palsy and the role of low dose granulocyte-colony stimulating factor injections," Restorative Neurology and Neuroscience, 2011, 17-22, vol. 29.

"Cord Blood for Cerebral Palsy: 1st publication of controlled trial," Parent's Guide to Cord Blood Foundation, Dec. 24, 2012.

Kyung et al.,: "Umbilical Cord Blood Therapy Potentiated with Erythropoietin for Children with Cerebral Palsy: A Double-blind, Randomized, Placebo-Controlled Trial," Wiley Online Library, 2013.

Lv, Y., et al.,: "Transplantation of human cord blood mononuclear cells and umbilical cord-derived mesenchymal stem cells in autism," Journal of Translational Medicine, 2013, 11:196.

Chez, M., et al.: "Safety and Observations in a Pilot Study of Lenalidomide for Treatment in Autism," Autism Research and Treatment, 2012, vol. 2012.

Boussi-Gross, et al.: "Hyperbaric Oxygen Therapy Can Improve Post Concussion Syndrome Years after Mild Traumatic Brain Injury," Randomized Prospective Trial, PLOS ONE, Nov. 2013, vol. 8, No. 11.

English Abstract of WO 2003061685.

\* cited by examiner

FIG. 1b: Pretreatment 5th digit
FIG. 1a: Pretreatment knuckle

FIG. 1d: Pretreatment rest of fingers
FIG. 1c: Pretreatment foot

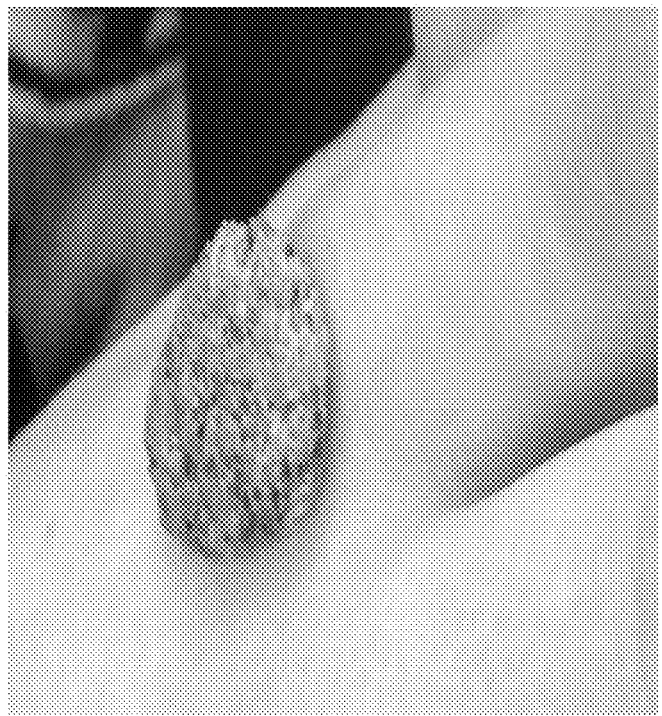
FIG. 2a: Large wart knuckle post treatment 2 weeks drier less erythema smaller

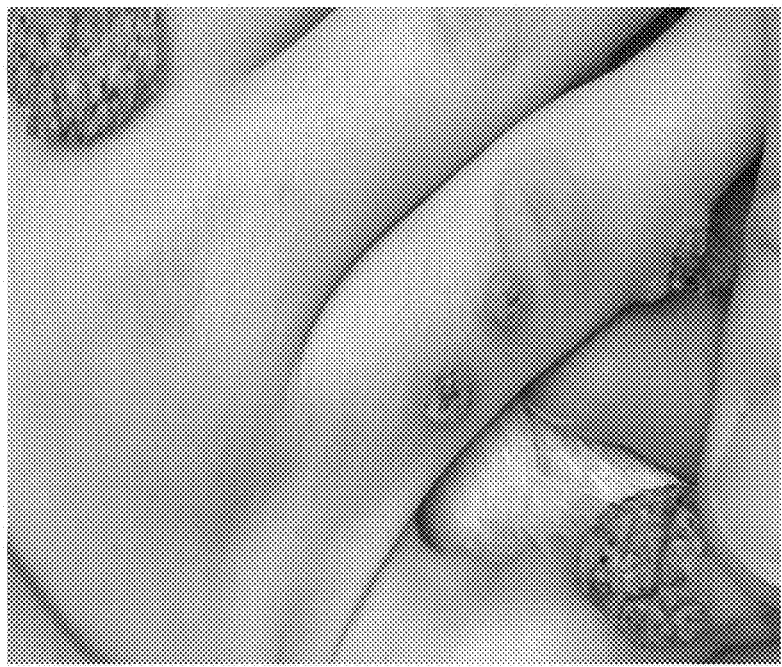
FIG. 2c : foot post treatment 2 weeks
FIG. 2d: fingers post treatment 2 weeks

TREATMENT OF WARTS IN NON-IMMUNOSUPPRESSED PATIENTS

This application claims priority to U.S. Ser. No. 62/117,119 filed on 17 Feb. 2015 in the U.S. Patent and Trademark Office, the entirety of which is incorporated herein by reference.

FIELD OF INVENTION

The present invention is directed to clinically-proven options for the treatment of warts that are resistant to pharmacotherapy. In particular, the present invention is directed to methods for treating warts comprising administering to a patient with warts a composition comprising 1) an autologous source of stem cells and/or 2) filgrastim, derivatives, and pharmaceutically effective salts thereof.

BACKGROUND OF INVENTION

Warts of neurocutaneous types can at times be treatment resistant. This includes common cutaneous warts and possibly venereal warts. In immunocompromised patients, treatment resistance is often the case. In non-immunocompromised cases, the reason for resistance to treatment is often unknown and may lead to chronic condition or surgical intervention.

Patients who have been treated for neutropenia with granulocyte agents, such as filgrastim, have noted at times warts resolved after this treatment in some cancer patients, however this was understood to be from treatment of neutropenia. No reports in non-cancer or non-immunosuppressed patients have been reported.

Filgrastim is a hematological growth factor that can release neutrophils and autologous stem cells from the bone marrow of an individual. It is known that filgrastim has an effect on a granulocyte-colony stimulating factor (GCSF) receptor in adult mammal neuronal stem cells. In addition, there is some prior scientific work discloses using filgrastim to harvest isolated stem cells for reimplantation or reinfusion in animal models of acute ischemia, hematological conditions, and acute trauma.

SUMMARY OF INVENTION

According to the present invention, a method for treating warts comprising administering to a patient with warts a composition comprising 1) an autologous source of stem cells and/or 2) filgrastim, derivatives, or pharmaceutically effective salts thereof.

BRIEF DESCRIPTION OF THE DRAWINGS

FIGS. 1A-1D shows a patient with multiple cutaneous warts on hands before filgrastim treatment according to the present invention.

FIGS. 2A-2D shows the patient of FIGS. 1A-1D after filgrastim treatment according to the present invention.

DETAILED DESCRIPTION OF INVENTION

The present invention is directed to treating warts in non-immunosuppressed patients with a composition comprising 1) an autologous source of stem cells and/or 2) filgrastim (commercially available from Amgen Inc. as NEUPOGEN®), derivatives, biological equivalent products, or pharmaceutically effective salts thereof.

A. Stem Cells

In a specific embodiment of the present invention, the composition may comprise an infusion utilizing an autologous source of stems cells (e.g., mesenchymal manufactured or donor derived, fat, tooth pulp, bone marrow derived or umbilical cord type (allogenic or autologous)). In a clinical trial in which Applicant served as the principle investigator, a non-immunosuppressed child with over 30 facial hand and foot cutaneous treatment-resistant warts had all warts resolved after a single autologous cord blood infusion with greater than (>) 1,000,000 cells/KG of CD34 component containing stem cells.

According to a specific embodiment of the invention, single or repeated autologous and Human Leukocyte Antigen (HLA) matched, donor-pooled cord blood treatments may be administered peripherally through intravenous administration and have from 100,000 to 100,000,000/KG of stem cells, with 1-10 million/KG of stem cells being experienced treatment-to-date.

B. Filgrastim

Applicant has also treated patients without known immunocompromise or neutropenia with 300 micrograms per day of filgrastim, subcutaneously for 3-5 days with a proven increase in stem cell component from laboratory blood tests confirming increased lymphocytic proportion of CD4 and CD34 type cells with treatment and elevation of total white blood cell count (WBC).

Pictures of pre-filgrastim treatment of a patient are shown in FIG. 1A (knuckle), FIG. 1B ($5^{th}$ digit), FIG. 1C (foot), FIG. 1D (other fingers). This patient had 26 warts on hands, fingers, toes, and feet.

Pictures of post-filgrastim treatment of the patient are shown 2 weeks after filgrastim treatment in FIG. 2A (knuckle), FIG. 2B ($5^{th}$ digit), FIG. 2C (foot), FIG. 2D (other fingers). After 7 days post-treatment 9 of 26 warts disappeared, and 19 warts were resolving within the first 10 days of treatment. In 3 months, any remaining warts either were gone or responded to laser therapy, which they were resistant to before filgrastim treatment. Complete resolution of warts within 3 months was also noted. The child also noted improved motor speech and social skills from which he was suffering delayed development.

In another patient (not pictured), within 3 weeks of single treatment with a composition comprising umbilical cord blood, 37 warts were completely eliminated on the hands and face of the patient.

Thus, according to a specific embodiment of the present invention, warts that are refractive to treatment that are cutaneous may be treated, improved, cured, or significantly diminished by single or multiple filgrastim injections at doses of about 100-500 micrograms per day for about 3-5 days subcutaneously.

According to the present invention, treatment with a composition may be repeated every 2 weeks, 4 weeks, 8 weeks, 12 weeks or monthly, quarterly, semi-annually, or annually depending on patient need and responses.

Although the specification is directed to patients who are non-immunosuppressed, it is believed that the present invention would also work in neutropenic or immunocompromised patients.

As used herein "substantially", "generally", "relatively", "approximately", and "about" are relative modifiers intended to indicate permissible variation from the characteristic so modified. It is not intended to be limited to the absolute value or characteristic which it modifies but rather approaching or approximating such a physical or functional characteristic.

References to "one embodiment", "an embodiment", or "in embodiments" mean that the feature being referred to is included in at least one embodiment of the invention.

Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

Although specific embodiments of the invention have been described herein, it is understood by those skilled in the art that many other modifications and embodiments of the invention will come to mind to which the invention pertains, having benefit of the teaching presented in the foregoing description and associated drawings.

It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

What is claimed is:

1. A method for treating warts, comprising:
    administering to a patient with warts a composition comprising filgrastim, derivatives, bioequivalents, and pharmaceutically effective salts thereof, and
    allowing the warts to be treated, wherein the warts disappear or respond to laser therapy;
    wherein said patient is non-immunocompromised and without neutropenia; and
    wherein said administering comprises an injection of filgrastim that is administered for about 3-5 days subcutaneously.

2. The method according to claim 1, wherein said warts are cutaneous warts.

3. The method according to claim 1, wherein said warts are veneral warts.

4. The method according to claim 1, wherein the injection is administered at a dosage of about 100-500 micrograms per day.

5. The method according to claim 1, wherein the injection may be repeated at least once.

6. The method according to claim 1, wherein the warts are treated and disappear.

7. The method according to claim 1, wherein the warts are treated and respond to laser therapy.

8. The method according to claim 1, wherein the composition comprises filgrastim.

* * * * *